(12) United States Patent
Campbell et al.

(10) Patent No.: US 6,596,531 B2
(45) Date of Patent: Jul. 22, 2003

(54) TWO STAGE METHOD FOR THAWING CRYOPRESERVED CELLS

(75) Inventors: Lia Hanson Campbell, Mount Pleasant, SC (US); Kelvin G. M. Brockbank, Charleston, SC (US); Michael J. Taylor, Mount Pleasant, SC (US)

(73) Assignee: Organ Recovery Systems, Charleston, SC (US)

( * ) Notice: Subject to any disclaimer, the term of this patent is extended or adjusted under 35 U.S.C. 154(b) by 0 days.

(21) Appl. No.: 09/835,819

(22) Filed: Apr. 17, 2001

(65) Prior Publication Data

US 2002/0012901 A1 Jan. 31, 2002

Related U.S. Application Data

(60) Provisional application No. 60/197,670, filed on Apr. 17, 2000.

(51) Int. Cl.[7] .............................. C12N 1/00; C12N 1/04; C12N 5/00; C12N 5/02; C12Q 3/00
(52) U.S. Cl. .................. 435/260; 435/243; 435/325; 435/395; 435/410
(58) Field of Search .............................. 435/325, 2, 1.3, 435/243, 3, 375, 395, 410, 260, 283.1, 284.1, 286.1

(56) References Cited

U.S. PATENT DOCUMENTS

| 4,199,022 A | | 4/1980 | Senkan et al. ............... 165/2 |
|---|---|---|---|
| 5,364,756 A | * | 11/1994 | Livesey et al. ............... 435/2 |
| 5,879,876 A | | 3/1999 | Wolfinbarger, Jr. et al. .. 435/1.2 |
| 5,964,096 A | | 10/1999 | Watson et al. ............... 62/78 |

FOREIGN PATENT DOCUMENTS

| EP | 0 834 252 | 4/1998 |
|---|---|---|
| WO | WO 96/30459 | 10/1996 |
| WO | WO 98/10231 | 3/1998 |
| WO | WO 99/18169 | 4/1999 |
| WO | WO 00/54584 | 9/2000 |

OTHER PUBLICATIONS

Hornung et al., "Cryopreservation of Anchorage–Dependent Mammalian Cells Fixed to Structured Glass and Silicon Substrates", Cryobiology, vol. 33, pp. 260–270, (1996).

Acker et al., "Influence of Warming Rate on Recovery of Monolayers with Intracellular Ice", World Congress of Cryobiology, Marseilles, France, p. 172, (1999).

Armitage et al., "The Influence of Cooling Rate on Survival of Frozen Cells Differs in Monolayers and in Suspensions", Cryo–Letters, vol. 17, pp. 213–218, (1996).

Watts et al., "Cryopreservation of Rat Hepatocyte Monolayer Cultures", Hum Exp. Toxicol., vol. 15(1), pp. 30–37, (1996).

Polge et al., "Revival of Spermatazoa After Vitrification and Dehydration at Low Temperatures", Nature, 164:666 (1949).

Lovelock et al., "Prevention of Freezing Damage to Living Cells by Dimethyl Sulfoxide", Nature, 183:1394 (1959).

Brockbank, "Essentials of Cryobiology", Principles of Autologous, Allogeneic, and Cryopreserved Venous Transplantation, Chapter 10, pp. 91–102, (1995).

Sicheri and Yang, Nature, 375:427–431, (1995).

Pasch et al., "Cryopreservation of Keratinocytes in a Monolayer", Cryobiology, vol. 39, pp. 158–168, (1999).

* cited by examiner

*Primary Examiner*—David M. Naff
*Assistant Examiner*—Deborah K. Ware
(74) *Attorney, Agent, or Firm*—Oliff & Berridge, PLC

(57) ABSTRACT

A two stage method of thawing cells from a cryopreserved state includes first warming the cells from a cryopreservation temperature to a transition temperature of at least −30° C. in a first, slow-warming stage by exposing the cells to an atmosphere having a temperature of less than 30° C., and once the cells have obtained the transition temperature, subsequently further warming the cells from the transition temperature by exposing the cells to a temperature of at least 32° C. in a second, rapid-warming stage. After the cells obtain the transition temperature in the first stage, the cells may be equilibrated at the transition temperature for a period of time prior to conducting the second stage warming. The method is particularly useful in warming cryopreserved cells attached to a fixed substrate. A thermal conduction device in association with the cryopreserved cells may also be used to further assist in the warming procedure.

15 Claims, 5 Drawing Sheets

TWO STAGE METHOD FOR THAWING CRYOPRESERVED CELLS

This application claims the benefit of Provisional Application No. 60/197,670 filed Apr. 17, 2000.

This invention was made with government support under grant Cooperative Agreement Number 70NANB7H307 1, awarded by the Department of Commerce. The government has certain rights in the invention.

BACKGROUND OF THE INVENTION

1. Field of Invention

This invention relates to novel two-step warming protocol for warming cryopreserved cells from a cryopreservation temperature. The invention also relates to the use of a heat sink in the warming of the cryopreserved cells.

2. Description of Related Art

Cryobiology may be defined as the study of the effects of temperatures of lower than normal physiologic ranges upon biologic systems. During the past half-century the fundamentals of the science of cryobiology have evolved to the point where low temperatures are now used extensively as a means to protect and preserve biological systems during enforced periods of ischemia and hypoxia. In practice, preservation is achieved using either hypothermia without freezing, or cryopreservation in which the aqueous system sustains a physical phase change with the formation of ice. Survival of cells from the rigors of freezing and thawing in cryopreservation procedures is only attained by using appropriate cryoprotective agents (CPAs) and in general, these techniques are applicable to isolated cells in suspension or small aggregates of cells in simple tissues. More complex tissues and organs having a defined architecture are not easily preserved using conventional cryopreservation techniques, which is principally due to the deleterious effects of ice formation in an organized multicellular tissue. Simply freezing cells or tissues results in dead, nonfunctional materials.

The modern era of cryobiology really began with the discovery of the cryoprotective properties of glycerol as reported by Polge et al., "Revival of Spermatazoa After Vitrification and Dehydration at Low Temperatures," *Nature*, 164:666 (1949). Subsequently, Lovelock et al., "Prevention of Freezing Damage to Living Cells by Dimethyl Sulfoxide," *Nature*, 183:1394 (1959), discovered that dimethyl sulfoxide was also a cryoprotectant, and despite the wide range of compounds now known to exhibit cryoprotective properties, it is still the most widely used compound to date.

A review of the principles of cryobiology can be found in Brockbank, *Principles of Cryopreserved Venous Transplantation,* Chapter 10, "Essentials of Cryobiology" (1995). A basic principle of cryobiology is that the extent of freezing damage depends upon the amount of free water in the system and the ability of that water to crystallize during freezing. Many types of isolated cells and small aggregates of cells can be frozen simply by following published procedures, but obtaining reproducible results for more complex tissues requires an understanding of the major variables involved in tissue cryopreservation. Major variables involved in tissue freezing include (1) freezing-compatible pH buffers, (2) cryoprotectant choice, concentration and administration, (3) cooling protocol, (4) storage temperature, (5) warming protocol and (6) cryoprotectant elution.

Most research in cryobiology has focused upon finding and testing new types of cryoprotectants. Many cryoprotectants have been discovered. See, for example, Brockbank, supra. Freezing protocols for placing cells in cryopreservation and warming protocols for removing cryopreserved cells from cryopreservation are presently fairly standardized in the art.

However, the present inventors believe that the existing one-step warming protocols may contribute to losses of cells upon warming from the cryopreserved state, particularly with respect to cells attached to a fixed substrate. What is desired is an improved procedure for warming cryopreserved cells, particularly cells fixed to an attached substrate, from the frozen state so as to achieve an increase in the number of viable cells recovered from cryopreservation.

SUMMARY OF THE INVENTION

It is therefore one object of the present invention to provide a novel procedure for warming cryopreserved cells from a cryopreserved state that minimizes loss of cryopreserved cells.

These and other objects are achieved by the present invention, which relates to a novel two-step warming procedure to warm cryopreserved cells from a cryopreservation temperature. This two-step warming procedure is particularly advantageous for warming cells attached to a fixed substrate.

The two stage method of thawing cells from a cryopreserved state includes first warming the cells from a cryopreservation temperature to a transition temperature of at least $-30°$ C. in a first, slow-warming stage by exposing the cells to a first environment having a temperature of less than $30°$ C., and once the cells have obtained the transition temperature, subsequently further warming the cells from the transition temperature by exposing the cells to a second environment having a temperature of at least $32°$ C. in a second, rapid-warming stage. After the cells obtain the transition temperature in the first stage, the cells may be equilibrated at the transition temperature for a period of time prior to conducting the second stage warming. The method is particularly useful in warming cryopreserved cells attached to a substrate, e.g., a fixed substrate.

A heat transfer device in association with the cryopreserved cells may also be used to further assist in the warming procedure, particularly when the cells are attached to a fixed substrate. In this regard, the invention also relates to a warming apparatus for cryopreserved cells, the apparatus including a vessel with which the cryopreserved cells are associated and a heat transfer device in association with the vessel.

DETAILED DESCRIPTION OF PREFERRED EMBODIMENTS

Figure 1:
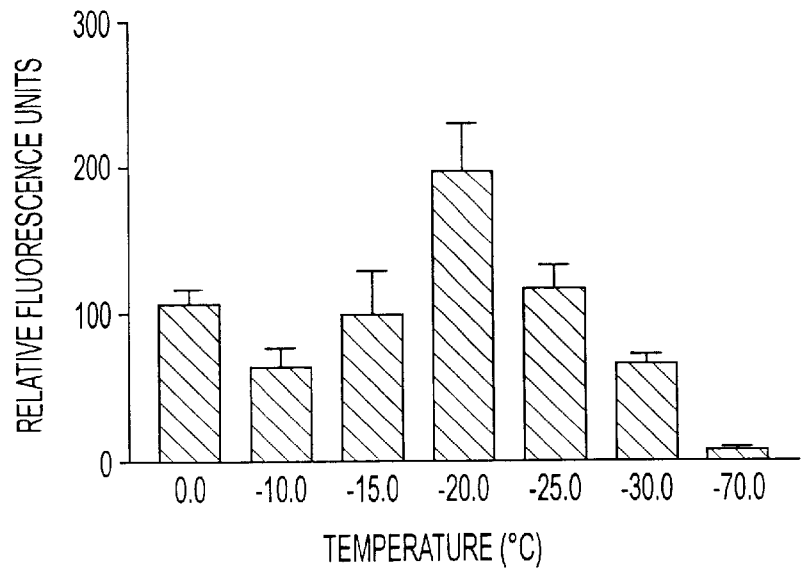
FIG. 1 is a graph of cell viability after variation of the transition temperature from slow to rapid warming of cryopreserved cell cultures.

Cryopreservation, i.e., the preservation of cells by freezing, in the present invention may be effected in any conventional manner. By "freezing" as used herein is meant temperatures below the freezing point of water, i.e., below 0° C. Cryopreservation typically involves freezing cells to temperatures well below freezing, for example to −80° C. or less, more typically to −130° C. or less.

The cells to be cryopreserved may be in suspension, may be attached to a substrate, etc., without limitation. In a preferred embodiment of the present invention, the cells that undergo cryopreservation are attached to a fixed substrate, for example the surface of a microtiter plate having multiple wells (although any suitable substrate may be used without limitation). The attachment of cells to a substrate is done by any technique known to practitioners in the art. See, for example, Pasch et al., "Cryopreservation of Keratinocytes in a Monolayer," *Cryobiology*, 39:158 (1999); Homung et al., "Cryopreservation of Anchorage-Dependent Mammalian Cells Fixed to Structured Glass and Silicon Substrates," *Cryobiology*, 33:260 (1996); Acker et al., "Influence of Warming Rate on Recovery of Monolayers with Intracellular Ice," World Congress of Cryobiology, Marseilles, France (1999); Armitage et al., "The Influence of Cooling Rate on Survival of Frozen Cells Differs in Monolayers and in Suspensions," *Cryo-Letters* 17:213 (1996); and Watts et al., "Cryopreservation of Rat Hepatocyte Monolayer Cultures," *Hum Exp Toxicol.*, 15(1):30 (1996), each incorporated herein by reference, describing techniques for attaching cells to a substrate. Cells are typically attached to the surface of a substrate in monolayers or less.

As the present invention relates to a warming method for rewarming cryopreserved cells from a cryopreserved state, the cells must first be in a cryopreserved state at a cryopreservation temperature. In this regard, any method of cryopreservation known to practitioners in the art may be used without limitation. The cryopreservation temperature should be less than −20° C., more preferably −80° C. or less, most preferably −130° C. or less.

In the method of cryopreservation, the cells are protected during cryopreservation by being brought into contact with a cryopreservation composition prior to freezing to the cryopreservation temperature. By being brought into contact with the cryopreservation composition is meant that the cells are made to be in contact in some manner with the cryopreservation composition so that during the reduction of temperature to the cryopreservation temperature, the cells are protected by the cryopreservation composition. For example, the cells may be brought into contact with the cryopreservation composition by filling the appropriate wells of a plate to which the cells to be protected are attached, by suspending the cells in a solution of the cryopreservation composition, etc.

The cells to be cryopreserved should also preferably be in contact with a freezing compatible pH buffer comprised most typically of at least a basic salt solution, an energy source (for example, glucose) and a buffer capable of maintaining a neutral pH at cooled temperatures. Well known such materials include, for example, Dulbecco's Modified Eagle Medium (DMEM). This material may also be included as part of the cryopreservation composition.

The cryopreservation composition may comprise any cryoprotective materials known in the art without limitation. Known cryoprotectant compounds include, for example, any of those set forth in Table 10.1 of Brockbank, supra, including, but not limited to, acetamide, agarose, alginate, 1-analine, albumin, ammonium acetate, butanediol, chondroitin sulfate, chloroform, choline, dextrans, diethylene glycol, dimethyl acetamide, dimethyl formamide, dimethyl sulfoxide (DMSO), erythritol, ethanol, ethylene glycol, formamide, glucose, glycerol, α-glycerophosphate, glycerol monoacetate, glycine, hydroxyethyl starch, inositol, lactose, magnesium chloride, magnesium sulfate, maltose, mannitol, mannose, methanol, methyl acetamide, methylformamide, methyl ureas, phenol, pluronic polyols, polyethylene glycol, polyvinylpyrrolidone, proline, propylene glycol, pyridine N-oxide, ribose, serine, sodium bromide, sodium chloride, sodium iodide, sodium nitrate, sodium sulfate, sorbitol, sucrose, trehalose, triethylene glycol, trimethylamine acetate, urea, valine, xylose, etc. The cryoprotectant compounds are preferably present in the cryopreservation composition in an amount of from, for example, 0.05 M to 6.0 M, preferably 0.1 to 3.0 M.

In a preferred embodiment of the present invention, the cryoprotectant composition includes at least one cyclohexanediol (CHD) compound, for example the cis or trans forms of 1,3-cyclohexanediol (1,3CHD) or 1,4-cyclohexanediol (1,4CHD), or racemic mixtures thereof, as a cryoprotectant compound. This preferred cryopreservation composition is described in Provisional Application No. 60/197,669 (Docket No. 105452) filed on Apr. 17, 2000, entitled "Cyclohexanediol Cryoprotectant Compounds," incorporated herein by reference in its entirety.

Preferably, the CHD compound is present in the cryopreservation composition in an amount of from, for example, 0.05 to 2.0 M, more preferably from 0.1 M to 1.0 M. The cryopreservation composition also preferably includes a solution well suited for organ storage of cells, tissues and organs. The solution can include the buffers discussed above. A particularly preferred solution is, for example, EuroCollins Solution comprised of dextrose, potassium phosphate monobasic and dibasic, sodium bicarbonate and potassium chloride.

The cryopreservation composition preferably includes both at least one CHD compound and at least one additional cryoprotectant compound.

Still further, the cryopreservation composition also may include an anti-freeze protein/peptide (AFP). AFPs also include anti-freeze glycoproteins (AFGPs) and insect anti-freeze, or "thermal hysteresis" proteins, (THPs). Naturally occurring AFPs are believed to be able to bind to the prism face of developing ice crystals, thereby altering their formation. For the fishes and insects in which these proteins occur, it means a depression of their freezing point so they are able to survive under conditions that would normally cause their body fluids to freeze. Any of the well-known AFPs may be used in the present invention in this regard. See, for example, Sicheri and Yang, *Nature*, 375:427–431, (1995), describing eight such proteins. Most preferably, the AFP may be, for example, AFPI (AFP type I), AFPIII (AFP type III) and/or AFGP. The AFP may be present in the cryopreservation composition in an amount of from, for example, 0.01 to 1 mg/mL, more preferably 0.05 to 0.5 mg/mL, of composition, for each AFP present.

Once the cells have been contacted with the cryopreservation composition, the cells may then be frozen for cryopreservation. The cooling for cryopreservation may be conducted in any manner, and may utilize any additional materials to those described above.

For example, the cooling (freezing) protocol for cryopreservation in the present invention may be any suitable type. Many types of cooling protocols are well known to practitioners in the art. Most typically, the cooling protocol calls for continuous rate cooling from the point of ice nucleation to −80° C., with the rate of cooling depending on the characteristics of the cells/tissues being frozen as understood in the art (again, see Brockbank, supra). The cooling rate may be, for example, −0.1° C. to −10° C. per minute, more preferably between −1° C. to −2° C. per minute. Once the cells are cooled to about −40° C. to −80° C. by this continuous rate cooling, they can be transferred to liquid nitrogen or the vapor phase of liquid nitrogen for further cooling to the cryopreservation temperature, which is typically below the glass transition temperature of the freezing solution (typically −130° C. or less).

Once cryopreserved, the cells will subsequently be rewarmed. Known warming protocols for cells and tissues have been one-step procedures in which the cryopreserved specimen is placed into a water bath at, for example, 37° C. to 42° C. Devices for more rapid one-step warming of cryopreserved biological materials have also been reported. These one-step warming protocols have been found by the present inventors to contribute to loss of viable cells upon rewarming of the cryopreserved cells.

Very few studies have been done examining the cryopreservation of cells on a fixed substrate. See, for example, Pasch et al., supra, Homung et al., supra, Acker et al., supra, Armitage et al., supra, and Watts et al., supra, for some of the few studies concerning cryopreservation of cells on a fixed substrate. The majority of studies, however, generally use cells in suspension.

For cell suspensions, the method of choice for thawing cryopreserved vials of cells is rapid one-step thawing at 37° C. Cryopreservation as an adherent monolayer upon a fixed substrate, however, simulates naturally occurring tissues, and tissues are also traditionally rewarmed using a one-step warming method. What few studies have been done with cells on fixed substrates make the assumption that because rapid thawing works well for cells in suspension, it will work well for cells attached to a substrate. However, the present inventors have discovered that this is not a correct assumption.

The warming protocol of the present invention involves a two-step warming procedure. In this two-step warming protocol, the cryopreserved cells (cryopreserved at the cryopreservation temperature) are removed from the cryopreservation freezer. Again, the cryopreserved cells are typically at a temperature of −130° C. or less. The cryopreserved cells are allowed to first slowly warm in a first environment in the first step of the two-step protocol. The environment is not required to undergo any special treatment or have any particular make-up, and any environment may be used, if desired, without restriction. Most preferably, the environment is a gaseous atmosphere, for example air. To effect the slow warming of the first stage, the environment should be at a temperature near normal room temperature. For example, temperatures of less than 30° C., preferably from 15° C. to 30° C., more preferably from 20° C. to 25° C., may be used.

The second step of the two-step warming procedure involves thawing the cells rapidly in a second environment having a warm temperature, for example above room temperature, and in particular, for example, on the order of 32° C. or more, preferably 32° C. to 50° C., more preferably about 37° C. Again, any suitable environment such as gas (air), liquid or fluid bed may be used as the second environment, a water bath having this temperature being most preferably used in effecting this rapid thawing.

The inventors undertook considerable work to identify the best transition temperature from the slow, first warming step to the more rapid, second warming step to allow for maximum cell viability. The results of this undertaking are summarized in FIG. 1.

FIG. 1 is a graph summarizing cell viability after variation of the transition temperature from slow to rapid warming of cryopreserved cell cultures. A10 cells were plated at $1 \times 10^4$ cells/well. The cells were placed in 1 M dimethyl sulfoxide (DMSO) on ice, cooled at −1° C./min to −80° C., and stored at −130° C. A two-stage warming protocol was employed for warming the cultures. The plates were removed from −130° C. and placed at ambient temperature in air (23° C.) for slow warming to temperatures ranging from −70° C. to 0° C., whereupon the plates were transferred to a 37° C. water bath and warm mannitol (0.5 M) solution was added to rapidly warm and thaw the cell cultures to ~0–4° C. The plates were put on ice and washed twice with 0.5 M mannitol and then with Dulbecco's Modified Eagle's Medium (DMEM) with 10% fetal calf serum (FCS).

The cells were left in DMEM plus 10% FCS and Alamar Blue (a non-invasive metabolic indicator from Trek Diagnostics) was added. Alamar Blue is a fluorescent dye that measures the oxidation/reduction reactions within cells, and thus is indicative of the overall viability of the cells after exposure to cryoprotective agents. A volume of 20 $\mu$l Alamar Blue was added to cells and the plate was incubated at 37° C. for 2 hours. Fluorescence from Alamar Blue was read in a fluorescent microplate reader (Fmax fluorescent microplate reader by Molecular Dynamics) using an excitation wavelength of 544 nm and an emission wavelength of 590 nm.

From this analysis, the second stage, fast warming step of the two-step warming protocol is preferably not begun until the cells have thawed to at least −30° C., preferably to at least −25° C., more preferably to at least −20° C. in the first stage, slow warming step. The cells are placed at a warmer temperature, for example about 37° C., to finish thawing the plate rapidly once the transition temperature has been reached.

Figure 8:
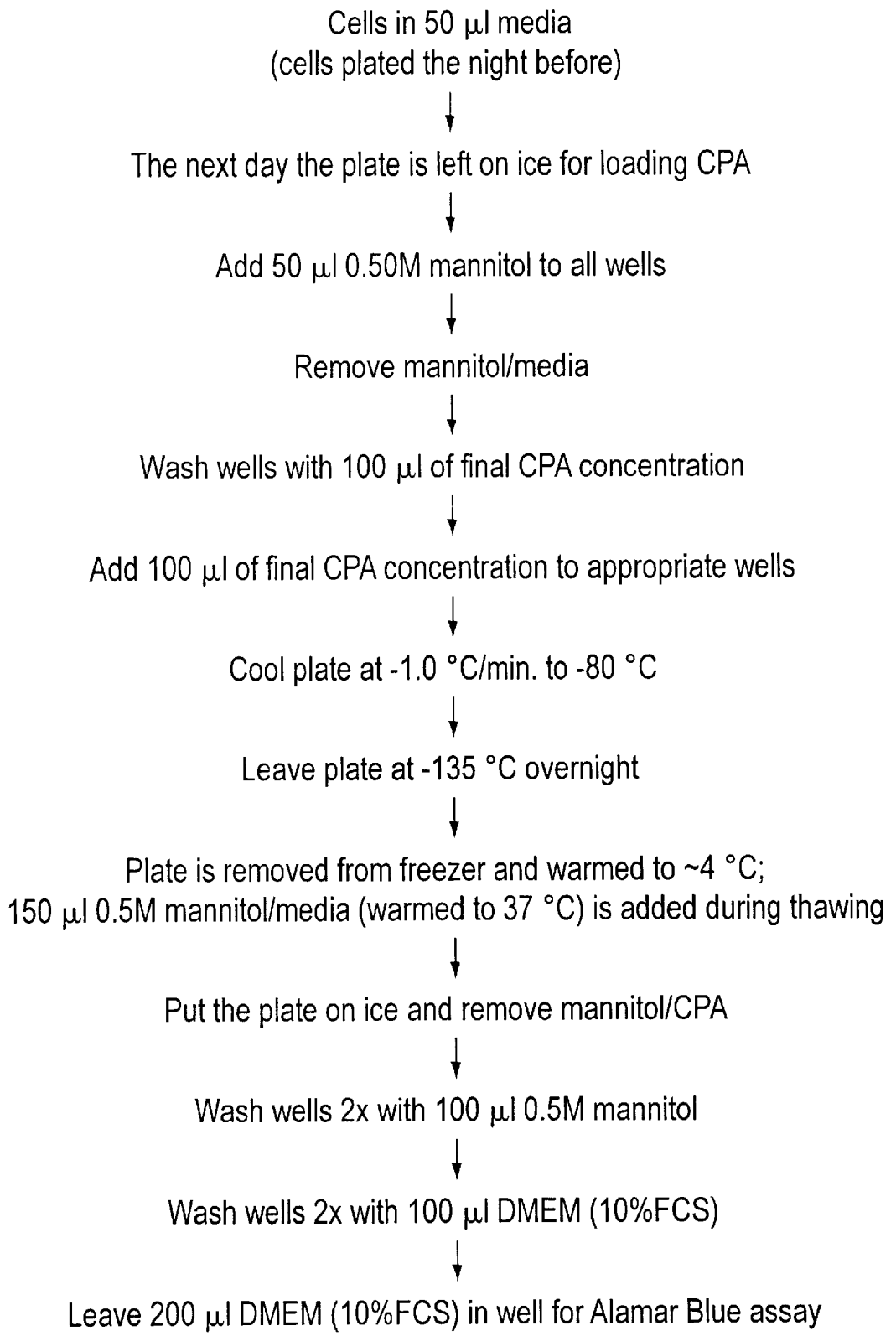
FIG. 8 is a flow chart summarizing a cryopreservation procedure that can be used in obtaining cryopreserved cells.

When this modified protocol was used to examine viability of cells after freezing and thawing using various concentrations of DMSO, cell viability was measured at ~25–30% for 1 M to 2 M DMSO (see FIG. 2), a considerable improvement from initial results of no cell survival. For FIG. 2, A10 cells were plated at $2.5 \times 10^4$ cells/well and exposed to 0 M to 6 M DMSO following the outline of FIG. 8. The plate was cooled at −1° C./min to −80° C. then stored at −130° C. The plates were warmed in two steps as described above. Data represent the mean (±SEM) of replicate samples frozen and thawed in a single plate.

Figure 3:
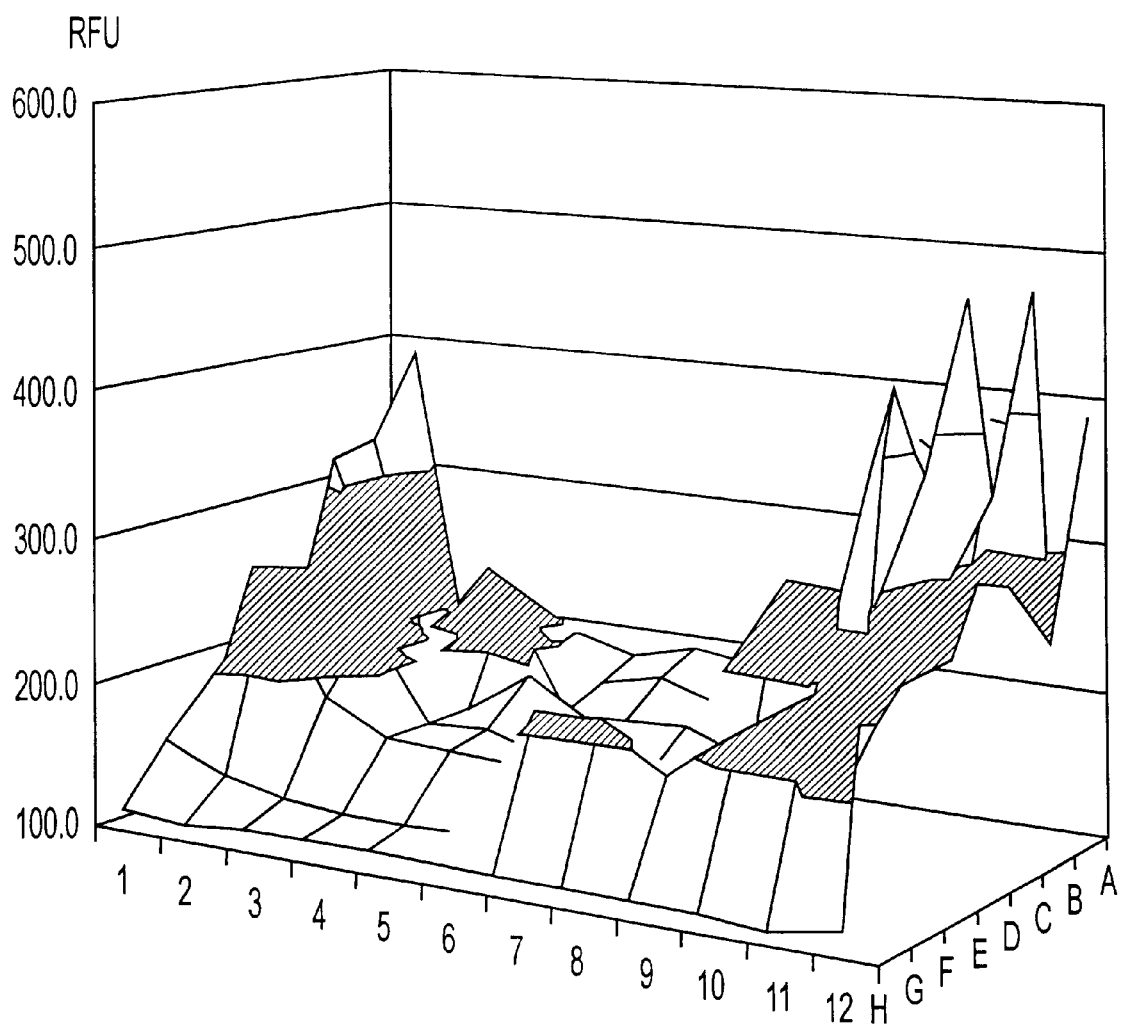
FIG. 3 is a three-dimensional graph of the variability of cell viability in a 96-well plate (12×8).

In FIG. 3, the variability of cell viability in a 96-well plate is illustrated. Cells were plated at a density of $2.5 \times 10^4$ cells/well, placed in 1 M DMSO on ice, and cooled to −80° C. at a controlled rate then placed at −130° C. The plate was warmed in two steps and the plate was read as described in FIG. 1. Data from wells with cells minus background were in rows A–G. The control wells (background) without cells were in row H. These results demonstrate that although the two-step warming protocol certainly is surprisingly advantageous, another hurdle is differential warming rates observed in different parts of a plate to which cells are attached. The right and left edges often warm faster than the middle during the slow warming step and consequently during the subsequent rapid thawing at 37° C. Thus, cell viability measured in the different areas of the plate reflects the differential warming rate, with some having higher viability than others.

For cells attached to a fixed substrate, concerns about sterility and possible contamination caused by warming the plate in a 37° C. water bath still remain with the novel warming protocol. In an effort to overcome these additional concerns, the invention further includes in embodiments the use of a method or device for uniform heat transfer that contacts, and preferably fits flush, with the bottom of a substrate to which cells are attached.

The cells, for example the cells attached to a substrate, e.g., a fixed substrate, are brought into contact and/or attached to a heat transfer device at any stage of the warming procedure. For example, the vessel or device containing the cells may be brought to contact a heat transfer device immediately upon removal from a cryopreservation environment, or only after completion of the first stage of the warming procedure.

Figure 4A:
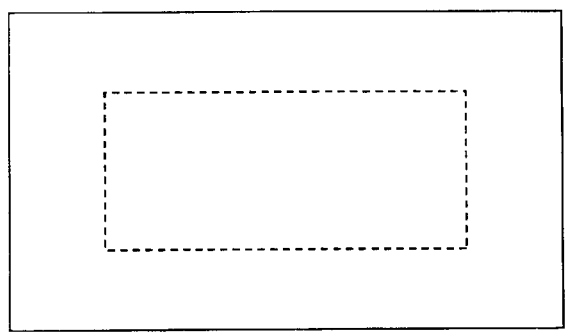
FIGS. 4A (top) and 4B (side) are schematics of a heat transfer (thermal conduction) device design according to the present invention.

The heat transfer device is most preferably of any a simple design that facilitates heat transfer between the device and the container of the cells. The heat transfer may be effected by, e.g., thermal conduction, convection or radiation, most preferably by thermal conduction. As shown in FIGS. 4A (top view) and 4B (side view), a heat transfer device is designed to have a raised portion that microtiter plates can be readily placed and fitted upon. The raised portion may be of any thickness such that the bottom of the microtiter plate can contact the device.

A suitable heat transfer device, i.e., thermal conduction device, may be a conventional heat sink, but is not limited thereto. Any material capable of effecting heat transfer may be used in any form without restriction. The heat transfer device may be comprised of a flexible or conformable material, including, for example, thermal conductive pastes or thermal conductive beads.

If fixed substrates other than microtiter plates are used, the heat transfer device should be designed so as to have a portion capable of readily contacting the fixed substrate.

Figure 4B:
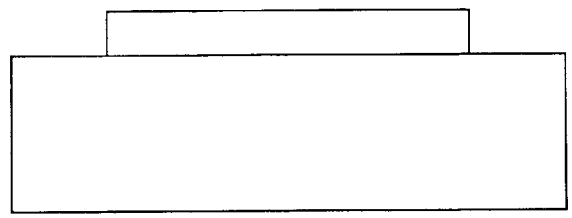

The heat transfer device may be made of any suitable material capable of transferring heat. For example, the device may be comprised of aluminum, which conducts heat efficiently. The base portion of the device such as shown in FIGS. 4A and 4B should preferably be of a thickness to provide sufficient mass for the heat transfer device to effectively hold heat and uniformly distribute it through the plate. For aluminum, the device should have a thickness of, for example, at least 1 inch. Greater thicknesses may be used.

As far as widths of the heat transfer device, any suitable width may be chosen. Preferably, widths are based upon the size of the fixed substrate that is to be placed into contact with the device so that the fixed substrate may sit completely against the device. Thus, different widths may be needed for different sized plates or cell containers.

The heat transfer device provides more uniform warming and also is able to retain a given temperature. The heat transfer device can be used within a hood or other sterile environment to minimize the risks of microbial contamination of the plate.

Figure 5:
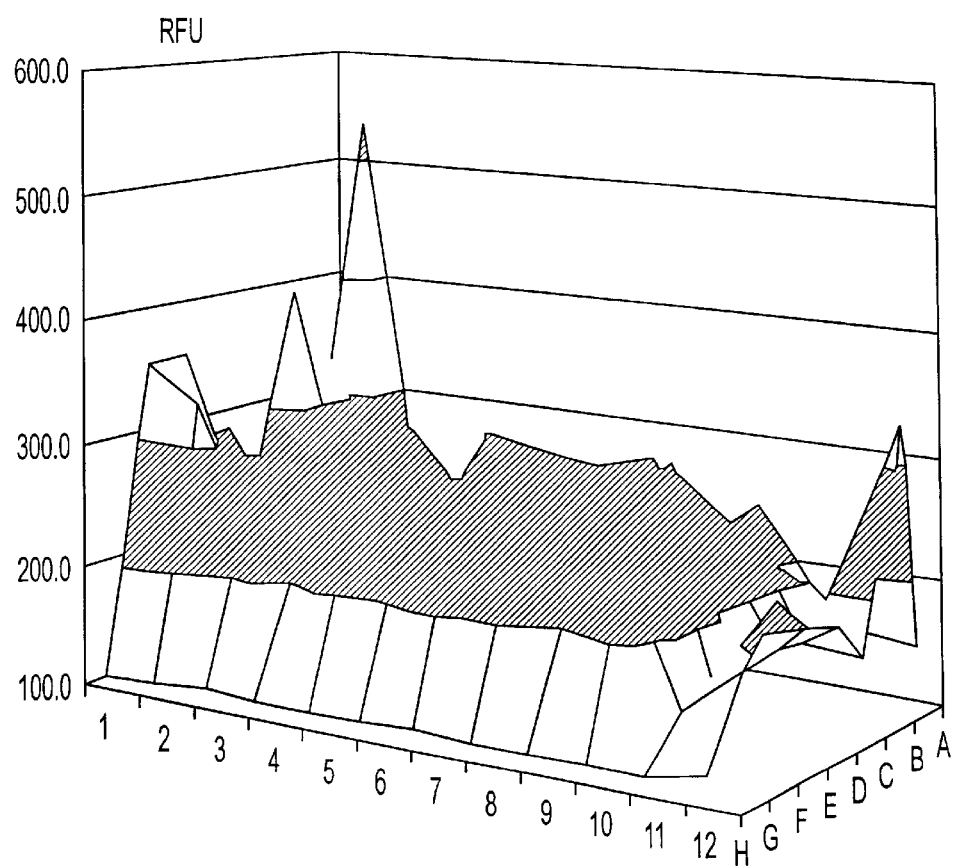
FIG. 5 is a three-dimensional graph of variability of cell viability in a 96-well plate using a thermal conduction device.

The use of the heat transfer device in conjunction with the two-step warming procedure further improves the uniformity of cell viability throughout most of the plate. See FIG. 5. In FIG. 5, the variability of cell viability in a 96-well plate using a heat sink is summarized. Cells were plated at a density of $2.5 \times 10^4$ cells/well, placed in 1 M DMSO on ice, and cooled to −80° C. at a controlled rate then placed at −130° C. The plate was warmed in two steps using a thermal conduction device at both temperatures and the plate was read as described above. Data from wells with cells minus background was in rows A–G. The control wells (background) without cells were in row H.

Figure 6:
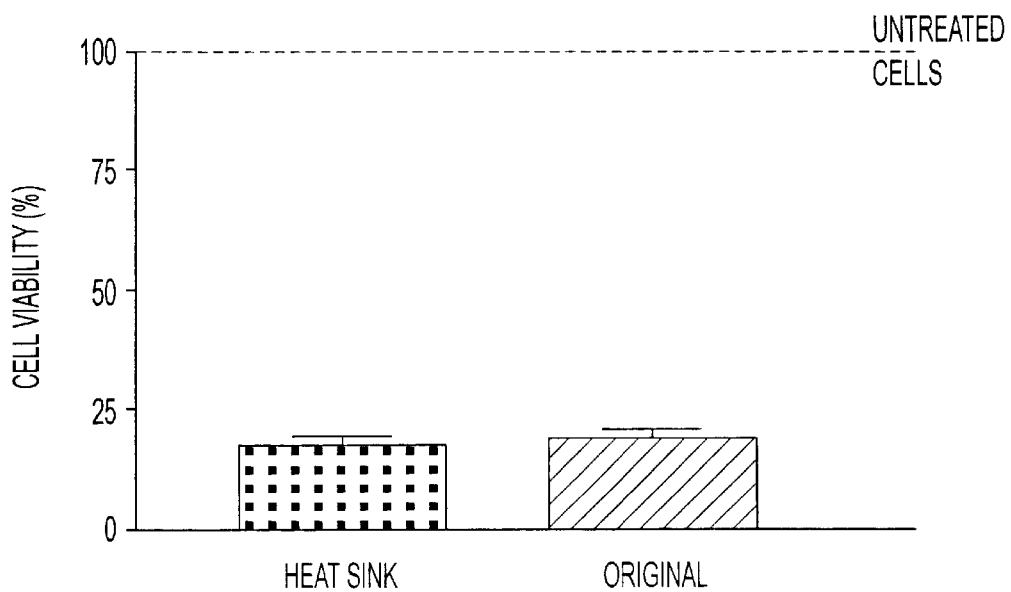
FIG. 6 is a graph of the percent cell viability of A10 cells after thawing.

While as shown in FIG. 6 the use of the thermal conduction device may not improve the overall cell viability upon rewarming from cryopreservation, the use of a heat transfer device still has the advantage of improving the uniformity of cell viability upon rewarming of cells attached to a fixed substrate, and also reduces the possibility of contamination. In FIG. 6, the percent cell viability of A10 cells after thawing is indicated. A10 cells were plated at $2.5 \times 10^4$ cells/well and cryopreserved in 1 M DMSO using a controlled rate freezer at a rate of −1.0° C./min. The next day the plates were thawed using the two step protocol described in the text (original) or using the same warming protocol with thermal conduction devices at 25° C. and 37° C.

In a still further embodiment of the invention, the first stage of the two-step warming procedure is conducted by removing the plate from cryopreservation at the cryopreservation temperature and allowing it to equilibrate in a freezer at the transition temperature (e.g., −20° C.) for a period of from, for example, 15 to 120 minutes, preferably 30 minutes. Following equilibration, the plate is rapidly thawed, for example at 37° C., in the second stage as discussed above.

Figure 2:
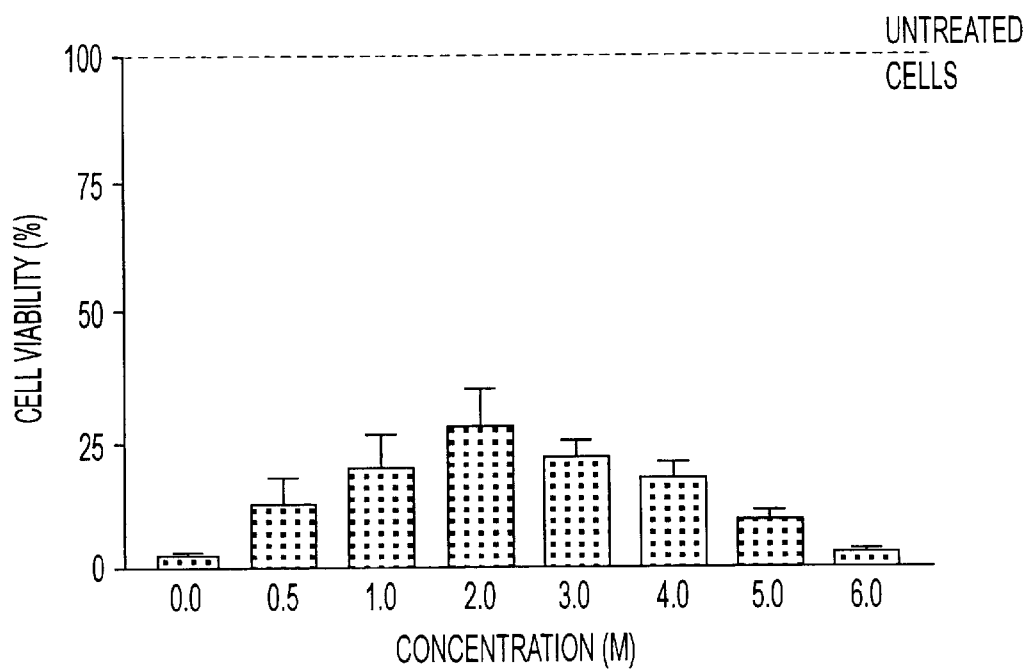
FIG. 2 is a graph of cell viability of adherent vascular smooth muscle cells cryopreserved in the presence of varying concentrations of DMSO.
Figure 7:
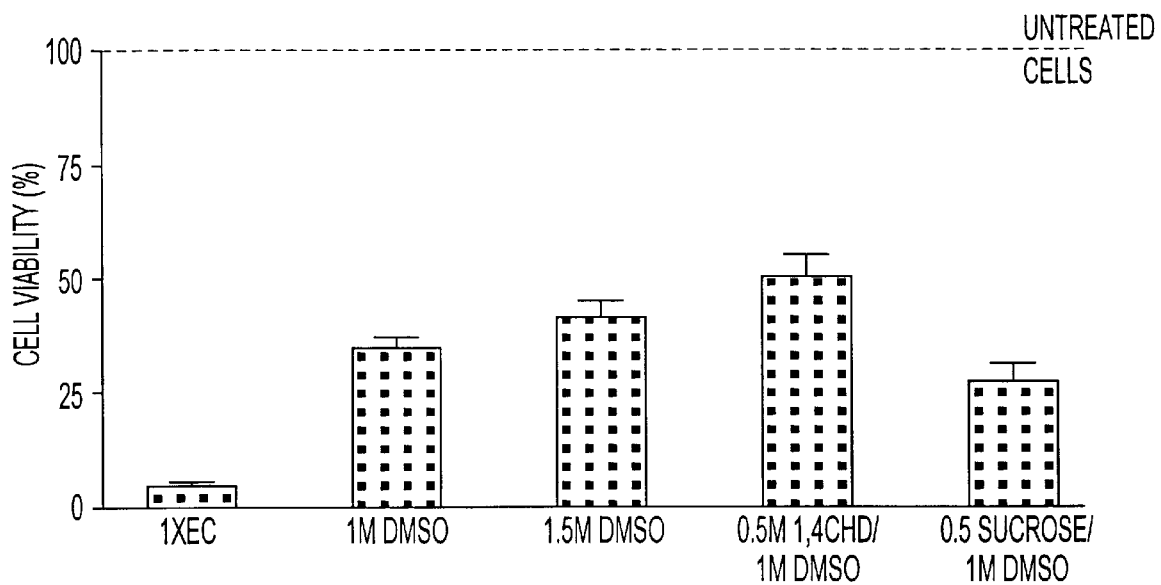
FIG. 7 is a graph of the percent cell viability of A10 cells after freezing and thawing on plates using various cryoprotectant agents.

With equilibration at the transition temperature, cell viability after exposure to 1 M DMSO increases significantly, from 25% to 40% (see FIGS. 2 and 7). In FIG. 7, the percent cell viability of A10 cells after freezing and thawing on plates is summarized for different cryopreservation compositions. A10 cells were frozen and thawed using the same protocol described for FIG. 1 above, except that the plate was allowed to equilibrate at ~20° C. before rapid thawing at 37° C. Data was normalized to untreated control cells (1XEC refers to EuroCollins solution used as a carrier vehicle solution for the cryoprotective agent) and is the mean (±SEM) of 12 replicates.

In summary, we have developed a two-step warming protocol for cells on a fixed substrate. This warming protocol is much less labor intensive and easier to perform than available alternatives. It is envisioned that any cell type could be adhered to a substrate and cryopreserved. These cryopreserved cells then could be thawed and be ready to use by the two step protocol for a variety of purposes. This thawing (rewarming) method enables the distribution of cryopreserved adherent cells in tissues or artificial constructs such that the end user of the material can consistently have a cryopreserved off-the-shelf product for their purposes. This will enable the end user to start their work in a fraction of the time that is now required to obtain tissues and/or grow, maintain, and plate cells for research experiments, bioassays or diagnostic purposes.

While this invention has been described in conjunction with specific embodiments thereof, it is evident that many alternatives, modifications and variations will be apparent to those skilled in the art. Accordingly, the preferred embodiments of the invention as set forth herein are intended to be illustrative only, and not limiting. Various changes may be made without departing from the spirit and scope of the invention as defined in the following claims.

What is claimed is:

1. A method of thawing cells from a cryopreserved state, comprising
   a first step of warming the cells from a cryopreservation temperature to a predetermined first temperature of at least −30° C. by exposing a vessel or device containing the cells to a first environment having a temperature of less than 30° C, and
   a second step of further warming the cells from the first temperature by exposing the cells to a second environment having a temperature of at least 32° C.

2. A method according to claim 1, wherein the predetermined first temperature is at least −20° C.

3. A method according to claim 1, wherein the first environment comprises air.

4. A method according to claim 3, wherein the air is at a temperature of from 20° C. to 25° C.

5. A method according to claim 1, wherein the cells are equilibrated at the first temperature for a period of time prior to the further warming in the second step.

6. A method according to claim 5, wherein the cells are equilibrated within a freezer at the first temperature.

7. A method according to claim 5, wherein the period of time is from 15 to 120 minutes.

8. A method according to claim 1, wherein the second environment comprises a water bath.

9. A method according to claim 1, wherein the second environment has a temperature of about 37° C.

10. A method according to claim 1, wherein the cells in the cryopreserved state are attached to a substrate.

11. A method according to claim 10, wherein the substrate comprises a plate having multiple wells therein.

12. A method according to claim 1, wherein the method further comprises bringing the vessel or device containing the cells into contact with a heat transfer device during an stage of the thawing.

13. A method of thawing cells attached to a substrate from a cryopreserved state, comprising
    a first step of warming the cells attached to the substrate from a cryopreservation temperature to a predetermined first temperature of at least −30° C. by exposing a vessel or device containing the cells to a first environment having a temperature of less than 30° C., and
    a second step of further warming the cells attached to the substrate from the first temperature by exposing the cells to a second environment having a temperature of at least 32° C.,
    wherein the method further comprises contacting the substrate with a heat transfer device during any stage of the thawing.

14. A method according to claim 13, wherein the substrate is a plate and the heat transfer device is made to contact a bottom of the plate.

15. A method according to claim 14, wherein the plate has multiple wells.

* * * * *